United States Patent [19]
Williams

[11] Patent Number: 5,629,474
[45] Date of Patent: May 13, 1997

[54] PRODUCTION OF A SENSOR FOR CARBON MONOXIDE OR WATER VAPOR INCLUDING A SEMI CONDUCTOR METALLIC OXIDE, CATALYST, AND RHEOLOGICAL AGENT

[75] Inventor: Edward W. Williams, Keele, Great Britain

[73] Assignee: Keele University, Staffordshire, England

[21] Appl. No.: 530,246

[22] PCT Filed: Mar. 29, 1994

[86] PCT No.: PCT/GB94/00658

§ 371 Date: Nov. 2, 1995

§ 102(e) Date: Nov. 2, 1995

[87] PCT Pub. No.: WO94/23289

PCT Pub. Date: Oct. 13, 1994

[30] Foreign Application Priority Data

Mar. 30, 1993 [GB] United Kingdom ............... 9306594

[51] Int. Cl.$^6$ .................................. G01N 27/12
[52] U.S. Cl. ............... 73/23.2; 73/23.31; 73/31.05; 73/31.06; 422/88; 422/94; 422/98; 334/34
[58] Field of Search .................. 73/23.2, 23.31, 73/31.05, 31.06; 338/34; 422/88, 94, 98

[56] References Cited

U.S. PATENT DOCUMENTS

| | | | |
|---|---|---|---|
| 3,901,067 | 8/1975 | Boardman, Jr. et al. | 73/31.06 |
| 3,933,431 | 1/1976 | Trujillo et al. | 73/864.82 X |
| 4,000,089 | 12/1976 | Senda | 73/31.05 X |
| 4,347,732 | 9/1982 | Leary | 73/31.05 |
| 4,388,272 | 6/1983 | Gesteland | 73/19.02 X |
| 4,453,151 | 6/1984 | Leary et al. | |
| 4,457,161 | 7/1984 | Iwanaga et al. | |
| 4,575,141 | 3/1986 | Burns | |
| 4,601,914 | 7/1986 | Barnes et al. | |
| 4,703,646 | 11/1987 | Müller et al. | 73/31.06 X |
| 4,786,476 | 11/1988 | Munakata et al. | |
| 4,958,514 | 9/1990 | Takami et al. | |
| 5,086,286 | 2/1992 | Yasukawa et al. | |
| 5,296,196 | 3/1994 | Takeshima | 73/31.06 X |

FOREIGN PATENT DOCUMENTS

| | | |
|---|---|---|
| 0059557 | 9/1982 | European Pat. Off. . |
| 182485 | 5/1986 | European Pat. Off. . |
| 0205777 | 12/1986 | European Pat. Off. . |
| 3519397 | 12/1986 | Germany ............... 73/31.06 |
| 3519435 | 12/1986 | Germany ............... 73/31.06 |
| 20854 | 1/1992 | Japan ............... 73/31.06 |
| 45321 | 2/1993 | Japan ............... 73/31.05 |
| 1280809 | 7/1972 | United Kingdom . |
| 1288009 | 9/1972 | United Kingdom . |
| 2248306 | 4/1992 | United Kingdom . |
| 2249179 | 4/1992 | United Kingdom . |
| WO93/08550 | 4/1993 | WIPO . |

OTHER PUBLICATIONS

Techniques and Mechanisms in Gas Sensing 1991 "Pattern Recognition in Gas Sensing", Gardner et al, pp. 347–379.
Solid Gas Sensors 1987, "Conduction and Gas Response of Semi–Conductor Gas Sensors", Williams, pp. 71–123.
Solid State Gase Sensors 1987, "The Role of Precious Metal Catalysts", Norris, pp. 124–138.
J. Chem. Soc., Faraday Trans. 1, 1987, "Tin Dioxide Gas Sensors", McAleer et al, pp. 1323–1346.
J. Chem. Soc., Faraday Trans. 1, 1988, "Tin Dioxide Gas Sensors", McAleer et al., pp. 441–457.
Electronics Ceramics: Properties, Devices and Applications, 1988, "Thick Film Technology", Cote et al, pp. 307 & 311.
Proc. Intl. Meeting on Chemical Sensors, 1983, "Sintered $SnO_2$ Sensor for Methane", et al, pp. 57–59.
Sensors and Actuators 1985, "Effect of $CH_4$, $SO_2$ and NO on the CO . . . ", Romppainen et al, pp. 271–279.
Fire Safety Journal 1991 "The Use of Low Power Carbon Monoxide . . . ", Harwood et al, p. 431.
Proc. Intl. Meeting on Chemical Sensors, 1983, "Sensitivity and Sintering Temperature of $SnO_2$ Gas Sensor," Murakami et al., pp. 18–23.

*Primary Examiner*—Hezron E. Williams
*Assistant Examiner*—Daniel S. Larkin
*Attorney, Agent, or Firm*—Nixon & Vanderhye P.C.

[57] ABSTRACT

A sensor to detect gases and vapors, particularly carbon monoxide and water vapor, at relatively low concentrations includes a substrate having a layer on a face of the substrate. The layer comprises a semi conductor metallic oxide (such as stannic oxide), a catalyst (such as platinum black), and a rheological agent (such as kieselguhr or sepiolite). The rheological agent induces porosity into the surface of the layer. The rheological agent affects the mixing and processing of the layer, and aids binding, resulting in a sensor with greater sensitivity and faster response.

20 Claims, 3 Drawing Sheets

PRODUCTION OF A SENSOR FOR CARBON MONOXIDE OR WATER VAPOR INCLUDING A SEMI CONDUCTOR METALLIC OXIDE, CATALYST, AND RHEOLOGICAL AGENT

FIELD OF THE INVENTION

This invention relates to a sensor for gases and vapours. For example, it may be used to detect carbon monoxide or water vapour. For convenience the invention will be described below with particular reference to the detection of carbon monoxide but it will be appreciated that its scope is not to be restricted thereto.

Detection of carbon monoxide is necessary in a number of different circumstances. For example, carbon monoxide is emitted when a fire starts to smoulder and can cause death before the fire begins to take hold. Most smoke detectors commercially available are based on one of two principles:

i) smoke scattering reducing the light intensity from a light emitting diode;
ii) monitoring the radiation from a radioactive source.

In both cases a considerable quantity of smoke is needed before the alarm is triggered and in neither case is there detection of the early emission of carbon monoxide.

BACKGROUND OF THE INVENTION

Sensors for carbon monoxide have been previously proposed and one well known type is based on the; use of a metallic oxide semiconductor, usually tin oxide $SnO_2$. The basic principle of their operation is the fact that the resistance of a layer of metallic oxide semiconductor changes in the presence of reactants such as organic vapours, carbon monoxide and even water vapour.

U.S. Pat. No. 4,453,151 discloses a sensor for detecting $H_2S$ which is made from a mixture comprising metal oxides, activators, dopants and binders and which includes a molecular sieve material, e.g. a zeolite, to provide porosity in the product on a molecular scale.

However, previously proposed tin oxide sensors have not been entirely successful in that they have suffered from problems such as lack of sensitivity to very small amounts of the specific gases to be detected, over-sensitivity to surrounding conditions, e.g. humidity, and lack of specificity in operation. They are too readily poisoned by other extraneous gases and have a slow recovery time after an initial detection. The present invention, therefore, aims to provide an improved sensor of increased selectivity that can be used particularly for the detection of carbon monoxide emissions and that, unlike most previous sensors, can also be operated at room temperature.

Accordingly, the invention provides a sensor to detect emissions of gas or vapour, which comprises a substrate having a layer of a composition comprising a semiconductor metallic oxide, a catalyst and a rheological agent to induce porosity into the surface of the layer, the semiconductor metallic oxide being indium oxide or tannic oxide and the catalyst is present in the composition in an amount of from 3 to 30% by weight.

The invention also provides a method of making a sensor.

The substrate, which should be a good electrical insulator, may be, for example, a sheet of glass or ceramic material. A film of the sensor composition from 100 nanometres 1 mm thick is preferably formed on the substrate by applying a paste of the oxide, catalyst and rheological agent in water to the substrate and annealing at a temperature of e.g. from 500° C. to 1000° C. to form a hardened layer.

The proportions of the ingredients of the covering layer composition may be, for example, 3 to 30% catalyst by weight, 5 to 20% by weight theological agent, if desired additives (well known per se) to change the electrical conductivity of the layer, e.g. in an amount of from 0.5–5% by weight; and the balance stannic oxide or indium oxide.

The catalyst is chosen to give specificity of the sensitivity of the sensor to the gas, e.g. carbon monoxide, to be detected. It is preferably platinum, particularly in the form of platinum black, i.e. finely divided platinum, but other catalysts, e.g. palladium, rhodimn, ruthenium, osmium and irridium may be used.

The rheological aid may be chosen from, for example, kieselguhr and sepiolite. It is preferable to use Kieselguhr, (or diatomaceous earth), which is a mass of hydrated silica. It provides an improved open-pore structure surface for the sensing area of the: sensor and increases the available surface area for reaction with the gas to be detected.

To prepare the usable sensor after the oxide layer has been applied to and annealed on the substrate, any suitable means may be utilized to provide electrodes to enable the required resistance measurements to be made. Thus, for example, silver, aluminium or tin electrodes may be formed on the surface of the stannic oxide film after masking desired portions of its surface. The electrodes may be applied by evaporation from a filament or a boat using a conventionally known vacuum system.

The invention is suitable for the manufacture of both so-called "thick film" sensors and "thin film" sensors. In the case of the former, the film thickness is usually from about 1 micron to 1 mm or higher whereas in the latter case it is usually up to about 1 micron.

Thick film sensors of the invention are particularly suitable for use as relatively low temperature devices in ambient temperature environments, and are suitable, e.g., for smoke detection in domestic situations and for personal, portable or fixed gas detectors in for example, coal mines. Thin film sensors, are usually employed as high temperature devices and are suitable, e.g., for process control and environmental monitoring in manufacturing operations involving gas furnaces.

Thick film sensors of the invention are particularly advantageous over known prior art thick film sensors in that they can be employed to operate at ambient temperatures whereas current commercial devices operate at high temperature and so normally require an additional power source, e.g. batteries, to provide the necessary heating.

Sensors of the invention display ohmic resistance and can be connected to conventional resistance measurement means incorporating warning means designed to be activated when the resistance of the sensor changes by more than a predetermined value.

The sensor or at least its chemically-sensitive semiconductor surface, should be housed to avoid light this being conventional practice with sensors of this general type. Thus they can, for example, be housed in housings of the type conventionally used for smoke detectors.

Although not wishing to be limited to any particular theory, it is believed that operation of the sensor is basically as follows. There is a surface reaction which comprises chemisorption of oxygen followed by desorption of oxygen in the presence of, e.g., CO gas. The CO gas is convened to $CO_2$ during the desorption and electrons are released so that the surface resistance decreases. The increased surface area of the sensor of the invention due to the induced porosity (porosity being the ratio of the volume of void space to the total volume) greatly improves the effectiveness of the sensor. It is also believed that water vapour may play a role in the surface reactions and so its presence, e.g. in normal humidity conditions of up to 90% relative humidity, is needed for maximum sensitivity.

Sensors of the invention have high sensitivity. They can detect less than 10 parts per million of carbon monoxide in air or nitrogen. They are very specific and, as shown below, react markedly to carbon monoxide emissions in contrast to a variety of other gases. They are stable and reproducible, and have long service life in comparison with known similar devices. They can be manufactured commercially at relatively low cost and can be of reduced size relative to comparable devices currently available.

Embodiments of the invention are now described by way of example only.

EXAMPLE 1

A thick film sensor was made as follows. Glass substrates of approximately 2.5×3.75 cms were cut to size from glass microscope slides. The substrates were cleaned to remove dust, oily deposits and other contaminants by rinsing in acetone and then water, followed by drying. The cleaned dry substrates were placed in an evaporation dish.

A sensor composition was made by thoroughly mixing the following ingredients:

|  | % by weight |
| --- | --- |
| Stannic oxide | 85 |
| Kieselguhr | 10 |
| Platinum black | 5 |

50 ml of distilled water was then added to the mixture and stirred until all the powder was dispersed to form a fine slurry.

The slurry was poured over the cleaned glass substrates, and the water slowly distilled off, leaving a thick film deposit of the sensor composition on each substrate. The layer was approximately 0.1 mm thick.

The coating layer so formed required annealing to convert it from a soft powdery consistency to a strong, hard layer firmly attached to the substrate. This was carded out in an oven at about 700° C. for about half an hour after which the sample was gradually cooled.

Tin electrodes were then deposited onto the surfaces of the annealed coatings using a vacuum deposition machine.

Firstly, the coated samples had their surfaces masked by a strip of PCB tape 0.5 mm wide attached centrally along their length. The masked samples were then placed in the chamber of the vacuum coater and when a vacuum of approximately $1\times10^{-6}$ Torr ($1.333\times10^{-4}$ newtons/sq. metre) was achieved, tin placed in a molybdenum boat through which current was passed, was evaporated and deposited onto the samples.

The products were thick film sensors having a centrally-extending exposed sensor surface between the deposited tin electrode.

EXAMPLE 2

Thin film sensors were made by preparing the dry powder sensor composition as described in Example 1. The powder was then mixed with a small amount of distilled water to form a stiff paste which was spread over a 5 cm square aluminium target. The mixture was allowed to dry in air for approximately 12 hours, the target was then placed within a larger 20 cm diameter target for installation into a sputtering system.

Glass slides were again used as substrates as for the thick film sensor and the coating was carried out as follows:

All films were produced by r.f. sputter deposition using a CVC 601 Sputter deposition system. The chamber has a base pressure of approximately $2\times10^{7}$ Torr ($2.666\times10-5$ newtons/sq. metre) and is fitted with a rotary manipulator for mounting and moving the glass substrates. The process gases used were argon and oxygen to partial pressures of 6 m Torr (0.8 newtons/sq. metre) and 2 m Torr (0.2666 newtons/sq. metre) respectively. R.f. power level for maintaining the sputtering plasma was 0.04 kW at room temperature. The sputtering process was carded out for a period of 60 minutes.

The coated substrates so prepared had a layer thickness of 100 nm.

Aluminium electrodes were deposited onto the surfaces of the coated substrates after masking had been carried out as in Example 1.

The electrodes were deposited using the sputtering technique.

Thick film sensors made as described in Example 1 above were tested as detailed below to show their selectivity and sensitivity as described below with reference to the accompanying drawings in which:

Figure 1:
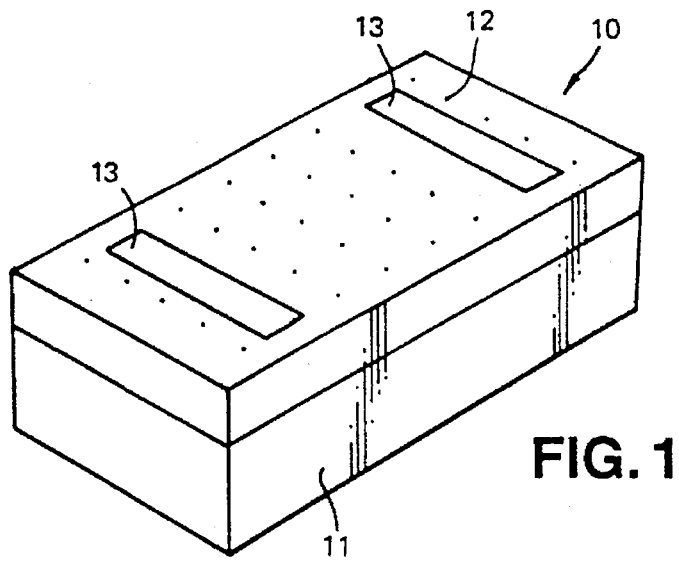
FIG. 1 is a diagrammatic representation in perspective view of a sensor of the invention.

DETAILED DESCRIPTION OF THE DRAWING
FIGURES

In FIG. 1, a sensor 10 of the invention has a substrate glass layer 11 on which has been formed a layer 12 formed of a semiconductor metallic oxide, catalyst and rheological agent. The surface of the layer 12 is porous. Electrodes 13 have been deposited on the surface of layer 12.

Sensor resistance was measured using a Keithley 618 electrometer, and the resistance $R_o$ of the sensors of the invention before exposure to CO was in the range 100 kΩ to 30 MΩ. Resistance was monitored during a simulated fire situation in which the sensor was located within a sealed chamber of volume $0.5m^3$; dry wood shavings were heated within the chamber using a filament passing a current of 1.5 A. The CO concentration was measured using a commercial CiTycel sensor, which operates on electrochemical principles, calibrated to the manufacturer's recommendations, and showed that the, arrangement described produced a maximum CO level of approximately 100 ppm within the chamber. Resistance readings for each sensor were initiated 5 minutes before the heater was switched on, in order to allow stabilisation in the ambient atmosphere of the chamber. The heater remained on for 20 minutes during which the CO concentration measured by the commercial sensor increased; it was then switched off and the CO concentration and sensor resistance monitored for a further period of approximately 1 hour. (The fact that the CO concentration does not return to zero is due to some residual CO adsorption on the CiTycel sensor.).

Figure 2:
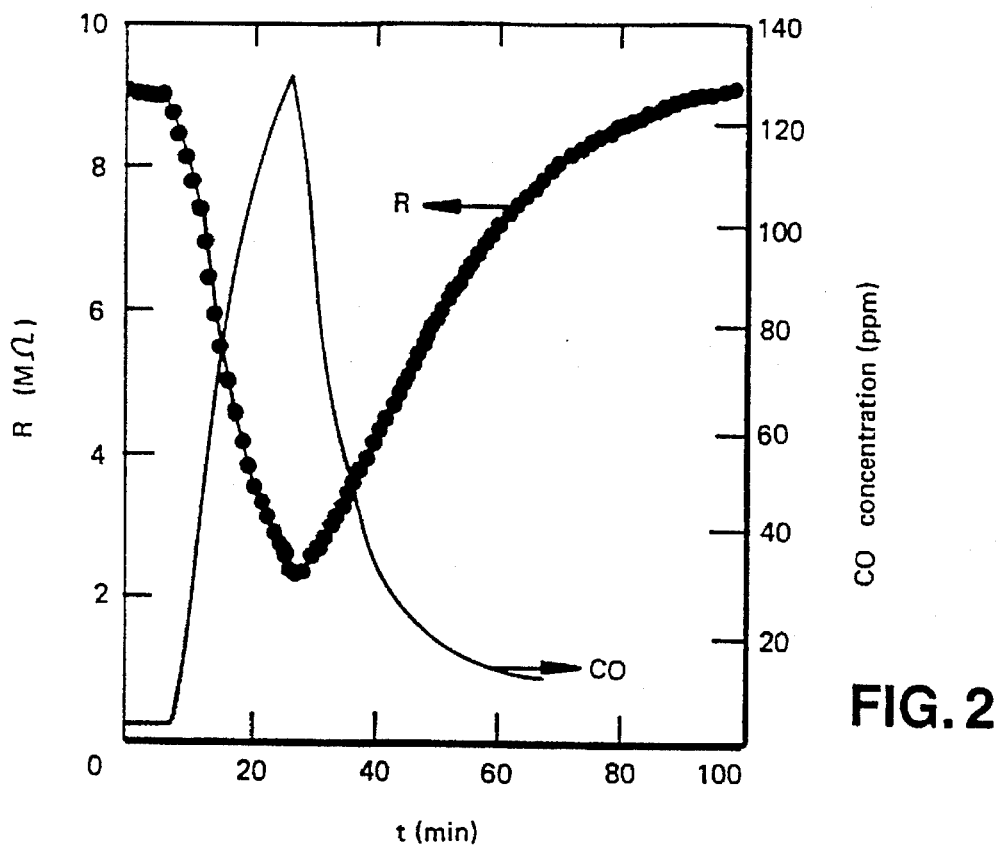
FIG. 2 is a graph of resistance at room temperature of a sensor of the invention and of CO concentration against time in a simulated fire situation.

FIG. 2 shows the variation of resistance R for a typical sensor over a time period of 100 minutes. Also shown is the varying CO concentration as measured with the calibrated commercial sensor. R remained constant during the initial 5 minutes stabilisation period, and then decreased rapidly during the following 20 minutes when the heater was turned on. After the heater was switched off there was a rapid decrease in the CO concentration and R began to increase. The minimum resistance of the sensor was after 25 minutes when the heater was switched off and the CO concentration was a maximum at approximately 130 ppm. It is clear that during the 20 minute period of CO emission the rate of change of resistance dR/dt is large and approximately constant.

Figure 3:
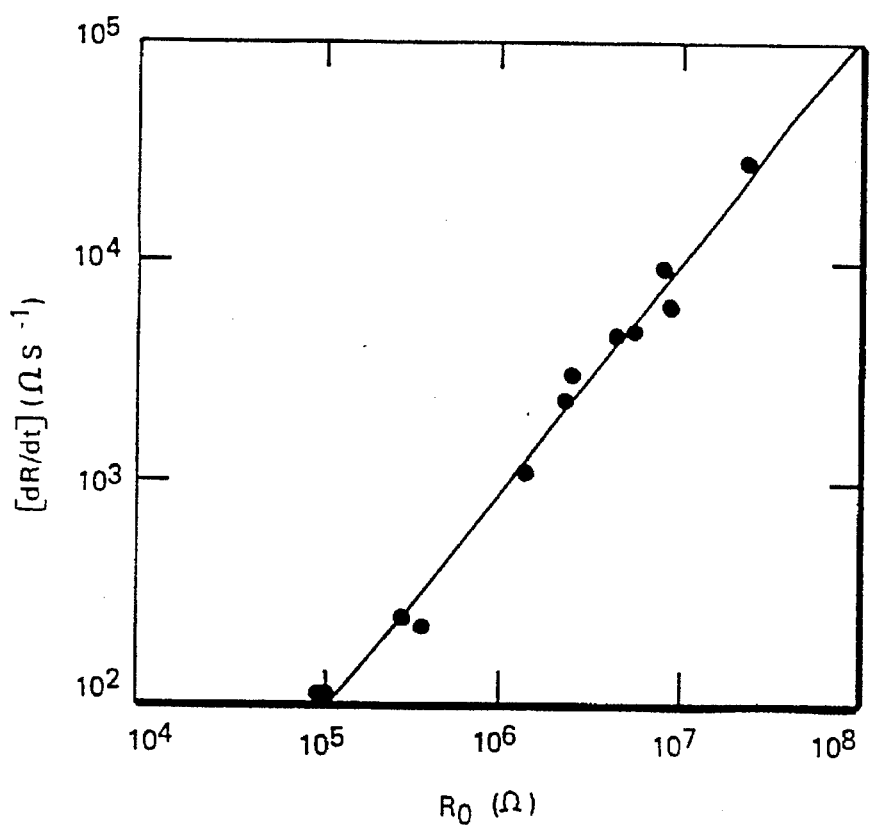
FIG. 3 is a graph showing the relationship at room temperature between average rate of change of resistance and the start resistance.
Figure 4:
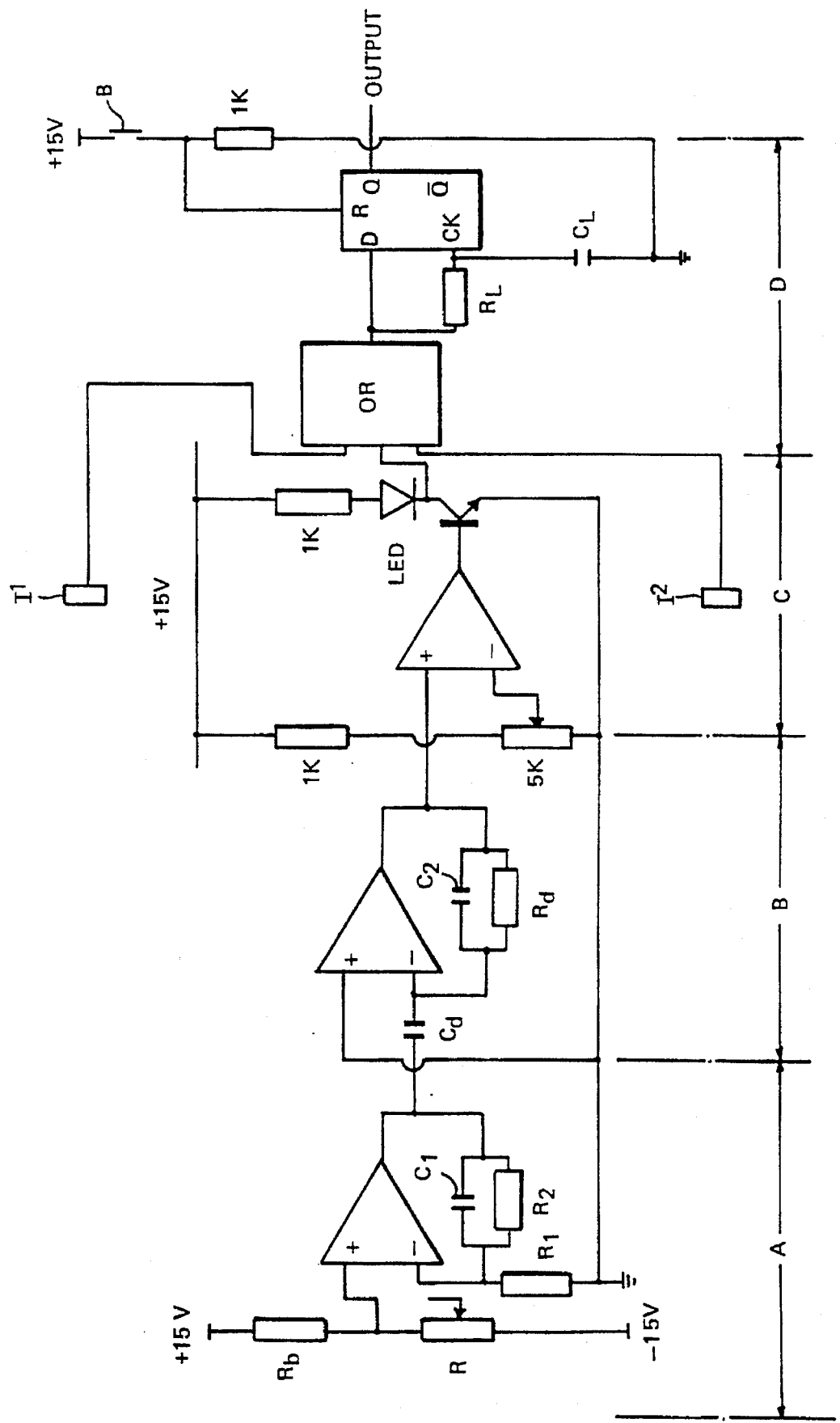
FIG. 4 is a circuit diagram for measuring the rate of change of three CO sensors in a sensor system.

In FIG. 3, the relationship between average rate of change of resistance [dR/dt] and the start resistance $R_o$ is shown. There is a clear linear relationship between log [dR/dr] and log $R_o$ with slope unity, and thus [dR/dt] is directly proportional to $R_o$ and is given by $$\left[\frac{dR}{dt}\right] = KR_o \quad (1)$$

where K is a proportionality constant. From FIG. 3 a value of $K=10^{-3}s^{-1}$ may be derived; this value is used in the design calculations for the resistor value $R_b$ in the electronic circuitry described below with reference to FIG. 4 and designed to operate in conjunction with sensor elements of the invention.

The maximum value of dR/dt was observed to occur at approximately 7.5 minutes after exposure to CO. This may be observed in FIG. 2 where the slope of the R-t curve is greatest at approximately 12.5 minutes from the start of measurements. The circuit was therefore designed to detect this high value of dR/dr. The rate of change of resistance due to CO is considerably higher than for other pollutants and false responses are very unlikely. The circuit design (FIG. 4) consists of four basic units: a bridge and amplifier 'A', a differentiator 'B', a comparator 'C' including an output device (LED) and simple logic circuitry 'D' to accept multiple inputs from separate sensors and for control of the alarm. The circuit requires at ±15 V dc power supply.

The simple bridge network consists of the sensor R and a fixed resistor $R_b$. The value of $R_b$ was chosen so that its value was approximately equal to the sensor resistance R at the time of maximum dR/dr. After exposure to CO the sensor resistance is given approximately by $$R = Ro - \left[\frac{dR}{dt}\right] t$$

Since [dR/dt] is related to $R_o$ via equation (1) above, the expected value of R may be simply estimated using t=450 s. Simple substitution of $K=10^{-3}$ $s^{-1}$ shows that the require, d value of $R_b \approx 0.55$ $R_o$. This value also ensures that the bridge amplifier is saturated at its maximum value until R decreases to a value where dR/dt is relatively high. This is necessary because the high gain needed in the non-inverting amplifier (1+ ($R_2/R_1$)) would otherwise lead to premature saturation before dR/dt attained the required value. The minimum value of the amplifier gain is dictated by the minimum rate of change of voltage detectable at the differentiator input. The differentiator produces an inverted output voltage proportional to the rate of change of input voltage with proportionality, constant (time constant) $R_d C_d$. Values of $R_d$ and $C_d$ are chosen to give a sufficiently high input voltage to the comparator. Two 0.1 µF capacitors $C_1$ and $C_2$ are incorporated into the circuit in parallel with the feedback resistors $R_2$ and $R_d$ respectively to reduce unwanted components of electronic noise. The comparator discriminates against voltages below its threshold voltage $V_p$, which is set to the calculated value expected at the differentiator output in the event of a fire. Typically it is of value 2 to 3 V. The comparator gives a digital output compatible with TTL logic, with logical output 1 when a fire is detected and 0 otherwise. An LED is also actuated in the event of a positive, response, to indicate the particular sensor giving rise to the signal. The logic circuitry includes an OR gate which enables monitoring of several sensors simultaneously, three being shown, one in full and two indicated as additional inputs $I_1$ and $I_2$. The gate outputs a logic 1 in the event of any one or more of the sensors being activated. Output signals from the OR gate are routed directly to the input of a positive-edge triggered D-type flip-flop and also connected via a delay to the clock input Ck. The flip-flop ensures that the alarm continues to sound after the fire has been detected until it is manually reset via the reset button B. A longer time delay may be introduced at the clock input by choosing suitable values of $R_L$ and $C_L$. This may be used to reduce the probability of false alarms due to transient conditions, since the high rate of change of sensor resistance needs to be present at both the start and finish of the delay period in order to activate the alarm.

Figure 5:
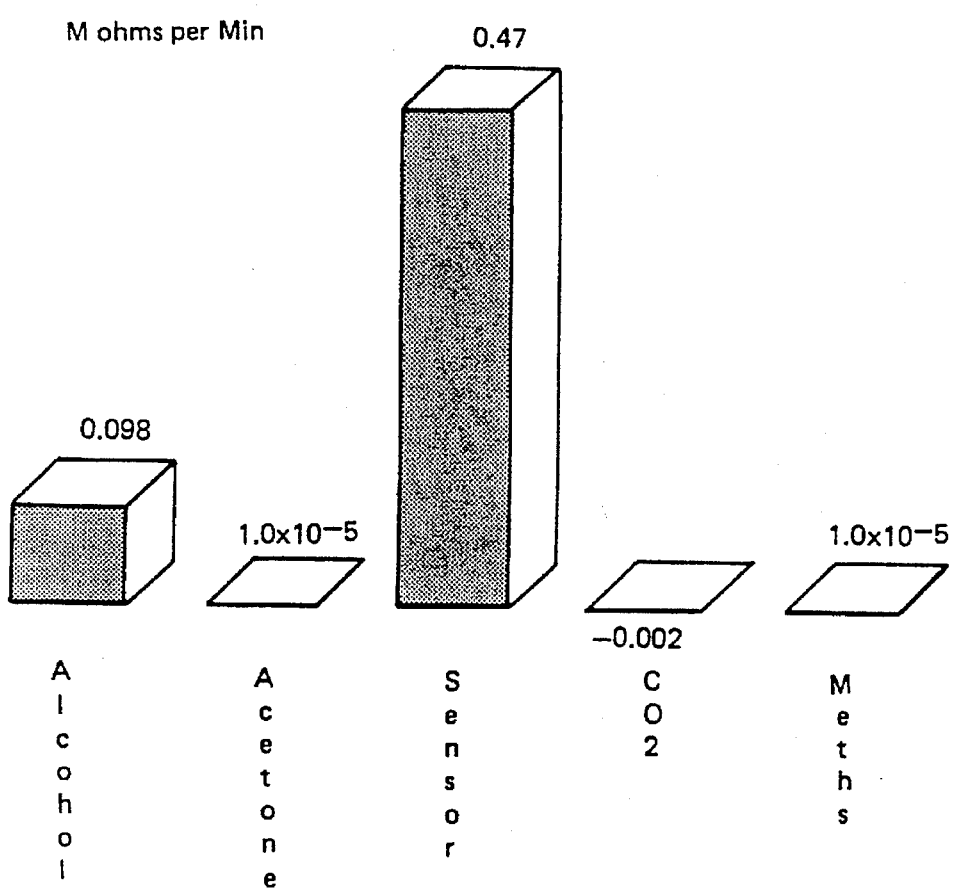
FIG. 5 shows the rate of change of the sensor reaction to exposure to a variety of chemicals compared with CO.

In FIG. 5, is shown the rate of change of the reaction of a sensor of the invention to a variety of chemicals compared with CO, the CO mode being marked "sensor". This clearly demonstrates that the sensor can be used to detect CO in a number of environments.

What I claim is:

1. A sensor to detect emissions of gas or vapor, which comprises a substrate having a layer of a composition comprising a semiconductor metallic oxide, a catalyst and a rheological agent to induce porosity into the surface of the layer, the semiconductor metallic oxide being indium oxide or stannic oxide and the catalyst is present in the composition in an amount of from 3 to 30% by weight.

2. A sensor according to claim 1, in which the substrate is a sheet of glass or ceramic material.

3. A sensor according to claim 1, in which the composition comprises by weight 5% to 20% rheological agent.

4. A sensor according to claim 1, in which the catalyst is of platinum, palladium, rhodium, ruthenium, osmium or irridium.

5. A sensor according to claim 3, in which the catalyst is platinum black.

6. A sensor according to claim 1, in which the rheological agent is Kieselguhr or sepiolite.

7. A sensor according to claim 1, in which the layer of the composition is from 1 micron to 1 mm thick.

8. A sensor according to claim 1, which is connected to resistance measurement means incorporating warning means designed to be activated when the resistance of the sensor changes by more that a predetermined value.

9. A sensor according to claim 8, in which the resistance measurement means comprises a bridge and amplifier, a differentiator, a comparator including an output device, and logic circuitry to accept multiple inputs from separate sensors and to control the warning means.

10. A sensor as recited in claim 3 wherein the rheological agent is kieselguhr or sepiolite.

11. A sensor as recited in claim 10 wherein the layer is from one micron to one millimeter thick.

12. A sensor as recited in claim 10 wherein the substrate is a sheet of glass or ceramic material.

13. A sensor as recited in claim 10 wherein the catalyst is platinum, palladium, rhodium, ruthenium, osmium, or irridium.

14. A sensor as recited in claim 10 wherein the semi conductor metallic oxide comprises stannic oxide.

15. A sensor as recited in claim 1 wherein the layer comprises about 85% by weight stannic oxide, about 10% by weight kieselguhr, and about 5% by weight platinum black.

16. A method of constructing a sensor to detect emissions of gas or vapor, the method comprising the steps of:

(a) forming a paste of a semi conductor indium oxide or stannic oxide, from 3–30% by weight of the catalyst, and a rheological agent, in water;

(b) applying the paste to a substrate to form a layer; and (c) annealing the layer at elevated temperature to form a hardened layer having a porous surface.

17. A method as recited in claim 16 wherein step (c) is practiced at a temperature of between 500°–1000° C.

18. A method as recited in claim 17 comprising the further step of masking the surface of the annealed hardened layer to leave exposed areas, and forming electrodes on the exposed area by deposition.

19. A method as recited in claim 18 wherein the electrodes are formed by evaporation from a filament or boat using vacuum, and wherein the deposit electrodes are formed of silver, aluminum, or tin.

20. A method as recited in claim 16 where, in step (a) is practiced by mixing as the rheological agent 5% to 25% by weight kieselguhr or sepiolite; and wherein the sensor is used to detect carbon monoxide or water vapor.

* * * * *

UNITED STATES PATENT AND TRADEMARK OFFICE
CERTIFICATE OF CORRECTION

PATENT NO. : 5,629,474
DATED : 13 May 1997
INVENTOR(S) : WILLIAMS, Edward W.

It is certified that error appears in the above-identified patent and that said letters patent is hereby corrected as shown below:

Column 1, line 63, insert -- to -- between "nanometres" and 1mm".

Column 3, line 45, replace "carded" with -- carried --.

Column 4, line 16, replace "carded" with -- carried --; and line 65, delete the ", [comma]" after "the".

Column 5, line 63, replace "requir.d" with -- required. --.

Column 8, line 2 of Claim 16, replace "the catalyst" with -- a catalyst --.

Signed and Sealed this

Twenty-sixth Day of August, 1997

Attest:

BRUCE LEHMAN

*Attesting Officer*  *Commissioner of Patents and Trademarks*